United States Patent
Ross et al.

[11] Patent Number: 5,470,351
[45] Date of Patent: Nov. 28, 1995

[54] METHOD AND APPARATUS FOR CREATING TATTOOS

[76] Inventors: Jerry Ross, 7615 Fielding, Detroit, Mich. 48228; Brian Sauvage, 2690 Golf Club Rd., Howell, Mich. 48843

[21] Appl. No.: 283,208

[22] Filed: Jul. 29, 1994

Related U.S. Application Data

[63] Continuation of Ser. No. 113,999, Aug. 30, 1993, abandoned.

[51] Int. Cl.⁶ ..................................................... A61N 5/00
[52] U.S. Cl. ........................... 607/95; 128/743; 132/319
[58] Field of Search ........................... 128/743, 846, 128/847–848; 607/95; 606/1, 116; 132/319

[56] References Cited

U.S. PATENT DOCUMENTS

| | | | |
|---|---|---|---|
| 1,748,403 | 2/1930 | Wentworth | 128/743 |
| 4,411,263 | 10/1983 | Cook | 607/95 X |
| 4,790,031 | 12/1988 | Duerer | 128/858 X |
| 4,793,003 | 12/1988 | Riedel et al. | 128/858 X |
| 4,903,840 | 2/1990 | So . | |
| 4,987,019 | 1/1991 | Jones . | |
| 5,052,418 | 10/1991 | Miller | 132/319 |
| 5,110,655 | 1/1992 | Engler et al. . | |
| 5,118,540 | 1/1992 | Hutchinson . | |
| 5,306,271 | 4/1994 | Zinreich et al. | 606/1 |

*Primary Examiner*—Angela D. Sykes
*Attorney, Agent, or Firm*—Gifford, Krass, Groh, Sprinkle, Patmore, Anderson & Citkowski

[57] ABSTRACT

A method and device for creating a suntan tattoo utilizing an applique is disclosed. The method includes cutting the applique from a two-ply blank formed of a flexible film sheet and a backing sheet. The flexible film has an adhesive coating on one side. Excess film is removed from the backing sheet. A transfer sheet having an adhesive coating is affixed over the applique and the backing sheet. The transfer sheet is then used to remove the applique from the backing sheet and apply the applique to the desired portion of the body. The transfer sheet is then removed from the skin, leaving the applique on the skin for exposure to tanning rays. After exposure to the tanning rays, the applique is removed, thus providing a precise suntan tattoo.

6 Claims, 1 Drawing Sheet

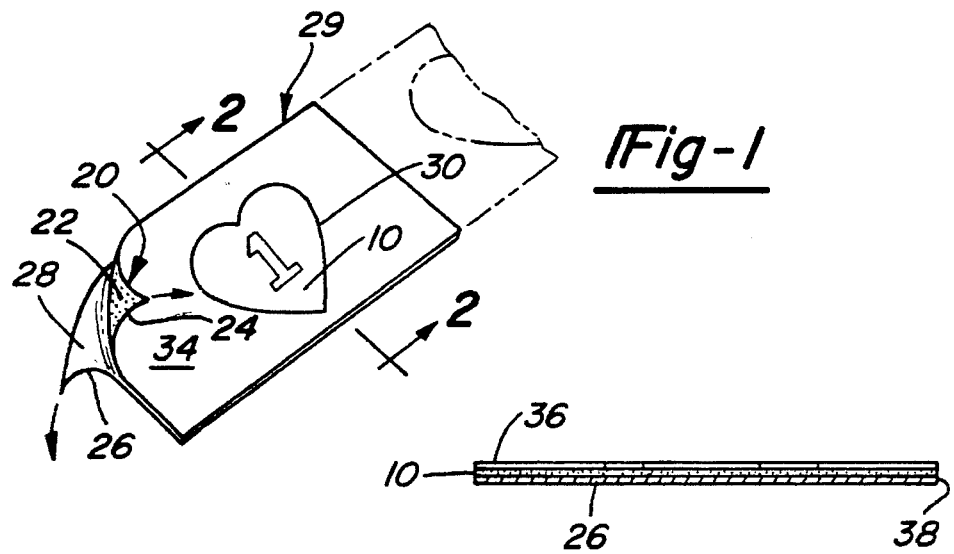
Fig-1
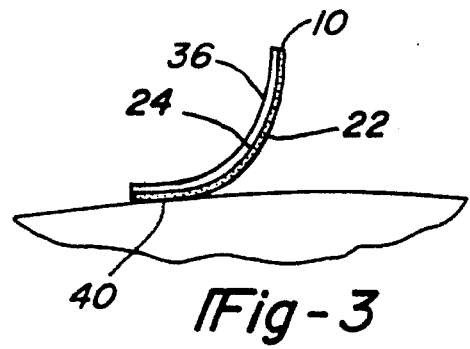
Fig-2
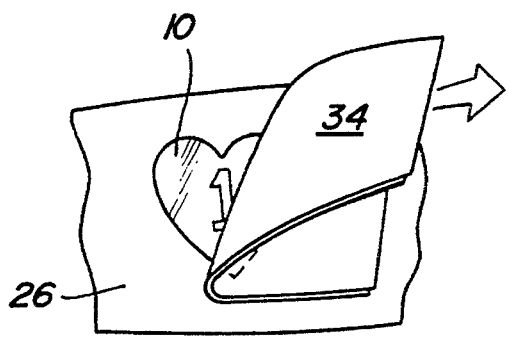
Fig-3
Fig-4
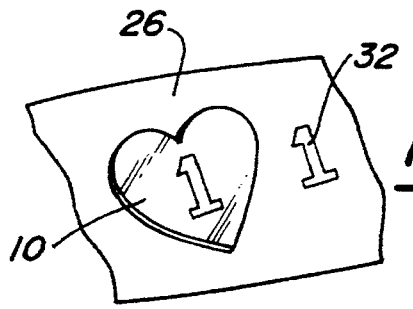
Fig-5
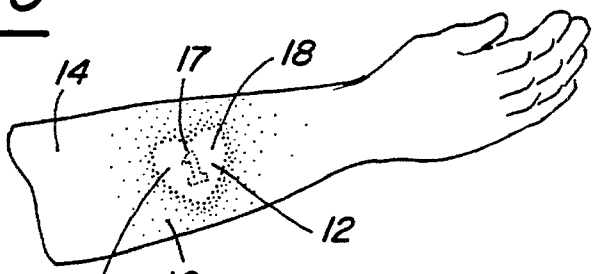
Fig-7
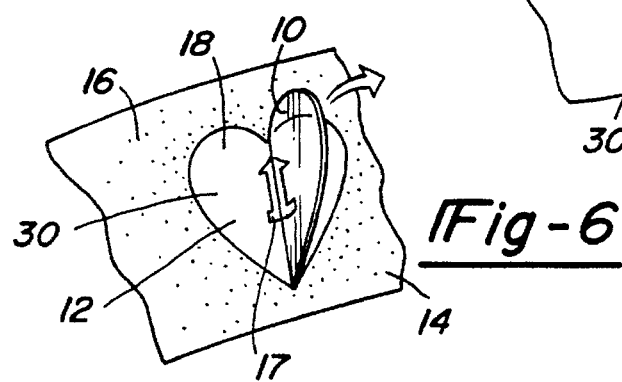
Fig-6

METHOD AND APPARATUS FOR CREATING TATTOOS

This is a continuation of application Ser. No. 08/113,999, filed on Aug. 30, 1993, now abandoned.

BACKGROUND OF THE INVENTION

I. Field of the Invention

The present invention relates to a device for creating an ornamental design or tattoo on a portion of human skin by blocking tanning rays of the sun with an applique. Also disclosed is a method of forming the applique and a method of use.

II. Background of the Invention

Recently there has been a fashion trend (particularly among the younger members of the population) to adorn the human body with tattoos. However, the tattooing procedure requires use of a needle and dye to affix a design permanently or semi-permanently in the skin of a part of the body, such as an arm or leg. Tattooing has many drawbacks, such as the permanency of the tattoo, as well as pain and possible infection associated with the application of the tattoo.

Likewise, it is known to adorn fingernails or toenails of a person with nail coverings such as nail polish or self-adhesive nail coatings, such as disclosed in U.S. Pat. No. 4,903,840. However, nail coverings and nail coatings are restricted to use on the nails. Likewise, it is known to apply paint directly to the body However body paints are not well suited for detailed ornamentation Thus, it is desirable to provide a manner of adornment of the body without the problems associated with tattoos and other methods of adornment.

SUMMARY OF THE INVENTION

The present invention is directed to a device for achieving self-expression by forming a design on the skin of a person by blocking the tanning rays of the sun to selected portions of the skin with an applique. The applique blocks the rays of the sun and creates a suntan tattoo through a color differential between tanned portions of the skin and untanned portions of the skin. Also disclosed is a method of forming the device and a method of use.

Disclosed ms a device for creating a suntan tattoo on a portion of a human body. Applicant's device includes an applique formed of a flexible sheet which is cut to a precise shape and has pressure sensitive adhesive on one side. The applique is advantageously formed of a hypo-allergenic material which blocks tile tanning rays of a light source. Additionally, the applique is advantageously provided for use in a three-ply sandwich wherein the applique is sandwiched between a backing sheet and a transfer sheet. The transfer sheet has an adhesive side which extends over the applique and backing sheet. The applique may be applied to the skin using the transfer sheet to remove the applique from the backing sheet and to position the applique on the skin Also disclosed is a method of use for suntan tattoos having a precisely defined shape Applicant's method includes providing a clear flexible film having an adhesive coating adhered to a backing sheet, cutting the film to a predetermined shape, discarding an excess portion of film, applying a transfer sheet having an adhesive coating on one side to cover the applique and backing sheet removing the applique from the backing sheet with the transfer sheet, applying the applique to a portion of skin on a human and removing the transfer sheet from the applique and skin, subjecting the skin containing the applique to the tanning rays of a light source for a period of time sufficient to tan the exposed skin and removing the applique from the skin thereby creating a suntan tattoo.

Also disclosed is applicant's of forming a blank having a first sheet of clear, flexible material having a backing sheet and a flexible sheet wherein the sheet member has an adhesive coating on one surface which is adhered to the backing layer and cutting through only the sheet member to form an applique having a predetermined shape and discarding the remaining portion of the flexible sheet.

DESCRIPTION OF THE DRAWING

FIG. 1 is a perspective view of a two-ply material formed of a flexible film having a design cut therein and a backing sheet;

FIG. 2 is an end view of a three-ply sandwich formed of the backing sheet, an applique and a transfer sheet;

FIG. 3 is a perspective view of the three-ply material and a portion of an arm;

FIG. 4 is a perspective view showing removal of the transfer sheet from the applique after the applique has been applied to the skin;

FIG. 5 is a perspective view of the applique in position for use during exposure to tanning rays;

FIG. 6 is a perspective view of the applique as it is being removed from the arm of the user; and FIG. 7 is a perspective view of the arm having a suntan tattoo created in accordance with the method of the invention.

DETAILED DESCRIPTION OF THE PREFERRED EMBODIMENTS

Referring to the drawings, and particularly FIG. 6, there-shown is an applique 10 for forming a suntan tattoo 12 in the form of a predetermined ornamental design on the skin of an arm 14 of a human. The applique is suitable for use on virtually any area of skin where there is no or little hair growth on the body of the human. The suntan tattoo 12 is defined of a an outer dark area 16 and an inner dark area 17 of skin which has been exposed to tanning rays of a light source (not shown), and a relatively light area 18 of skin which has been covered by the applique 10 during exposure to the tanning rays and is therefore lighter in color than the dark areas 16, 17 of skin. The applique 10 may be formed in such a way as to provide a tattoo in a precise shape forming a pattern, words, or logo. As will be discussed below, the tattoo can either be "tanned in" or "tanned out".

In the preferred embodiment, of the invention as shown in FIG. 1, the applique 10 is formed of a thin polyethylene film 20 approximately 3 mil (0.03 mm) thick. One side of the film 20 is provided with a hypo-allergenic, pressure sensitive acrylic adhesive coating 22. An opposite side 24 of the film has a smooth matte finish. In the preferred embodiment the film 20 is transparent, however, the film 20 must be capable of blocking the tanning rays of a light source, such as the sun or ultraviolet lamp. Suitable polyethylene film of this type is available for use in medical applications from 3M Health Care of St. Paul, Minn. The film 20 is supplied as a two-ply material with the film attached to a backing sheet 26. This two-ply material is known as Product No. 1525-L, Plastic Medical Tape On Liner.

As shown in FIGS. 1 and 2, the backing sheet 26 is a polyethylene coated bleached craft paper having a smooth silicone coating on an inner side 28 of the backing sheet 26 such that the polyethylene film 20 may be easily removed from the backing sheet 26.

As shown in FIG. 1, a desired design such as a heart 30 containing a Numeral 1, is formed on the polyethylene film by a suitable method such as die cutting from a blank 29 formed of the backing sheet 26 and a film 20. The die cutting procedure is performed in such a manner that only the film 20 is cut. Because the film is die cut, very precise applique members may be formed to provide attractive and well defined suntan tattoos After the design is die cut through the film 20, one portion of the film forms the applique 10 and the outer portion 34 of the film surrounding the applique portion and portion 32 forming the Numeral 1 form excess or scrap material. The outer portion 34 and inner portion 32 of the cut film are removed or peeled from the backing sheet 26 as shown in FIGS. 4 and 5, leaving the applique 10 on the backing sheet 26. The applique 10 may be formed to "tan out" so that a light area of skin is formed within a surrounding tanned area, as shown in forming the heart 30, as shown in FIG. 4. The applique 10 of the tattoo may also be formed to provide a circumferential border of tanned skin to define a "tanned in" portion, such as the Numeral 1 formed within the heart 30. The may be of any desired shape. Words, slogans, or designs can be formed by providing an applique 10 which either "tans out" or "tans in" the desired ornamental design.

As shown in FIG. 2, a transfer sheet 36 is placed over the applique 10 and backing sheet 26 to form a sandwich 38. Because the film 20 used for the applique 10 is quite thin and the applique 10 has adhesive on one side, it is frequently difficult to place the applique 10 directly on the skin of the user without crumpling or folding of the applique. To apply the applique 10, the user removes the backing sheet 26 from the sandwich 38 (FIG. 2) leaving the applique attached to the transfer sheet 36 by the adhesive coating 22 of the transfer sheet 36. The transfer sheet 36 and applique 10 are then applied to a portion of the user's body, such as a leg or arm 40, as shown in FIG. 3.

Thus, the transfer sheet 36 facilitates transfer of the applique 10 from the backing sheet 26 to the skin. In the preferred embodiment, the transfer sheet 36 is formed of a plastic tape having an adhesive coating on one side 40. A suitable material for the transfer sheet is known as "Premask" and is available from American Biltrite of Moorestown, N.J. 08057.

The transfer sheet must be larger than the applique so that there is a border or area which can be grasped without contact between the user's hand and the applique. It has been found that any contact between the user's hands and the adhesive of the applique will greatly diminish the ability of the adhesive to maintain the applique in position on the skin of the user. Once the sandwich 38 has been prepared, the outside surface of the transfer sheet is colored with a pencil, crayon, or the like, to produce an outline of the applique. In this way, the pattern of the applique is "embossed" on the transfer sheet to permit a consumer to discern the shape of the design of the applique. Thus, the sandwich 38 may be placed in clear packaging so that the consumer can see the shape of the applique.

The transfer sheet 36 is then removed from the arm 14, leaving the applique 10 affixed to the arm 14 ready for exposure to tanning rays. Because the applique 10 is formed of a thin, clear hypo-allergenic material, the applique 10 can remain in position on the skin for a number of days. After sufficient exposure of the arm 14 with the applique 10 to the tanning rays, a color differential is provided between the exposed area of the skin 16, 17 and the lighter area 18 of the skin covered by the applique, as shown in FIG. 7. After a desired amount of tanning has occurred, the applique 10 is peeled from the skin, as shown in FIG. 6, to provide a suntan tattoo 12 shown in FIG. 7.

Various modifications and alterations of this invention will become apparent to those skilled in the art without departing from the scope and spirit of this invention.

What is claimed is:

1. A device for forming an ornamental design on a portion of a human body which has been exposed to tanning rays of a light source, said device comprising:

a flexible sheet member being adapted to block the tanning rays from the light source having a top surface and a bottom planar surface having an adhesive coating fully covering said bottom planar surface, said sheet member having means for forming a predetermined non-utilitarian ornamental shape, said means including a peripheral edge formed on said sheet member, said sheet member adapted for affixation to said portion of said human body whereby said shape is formed on said body after exposure to tanning rays from the light source;

a transfer sheet, having an adhesive coating on one side;

a backing sheet having a smooth surface to which said bottom planar surface of said sheet member and said adhesive coating of said one side of said transfer sheet are detachably mounted, said sheet member being sandwiched between said backing sheet and said transfer sheet, said bottom planar surface of said sheet member and said adhesive coating of said transfer sheet contacting said smooth surface of said backing sheet for easy removal of said backing sheet.

2. The device of claim 1, wherein said flexible sheet member is formed of a light-blocking material.

3. The device of claim 2, wherein said sheet material is formed of a color which contrasts with said transfer sheet.

4. The device of claim 1, where said backing sheet is transparent such that the said ornamental shape of said sheet member can be seen through said backing sheet.

5. A method of forming an applique for creating an ornamental design on a portion of a wearer's body, said method comprising:

forming a two-ply blank having a backing sheet and a flexible sheet member, said sheet member having an adhesive coating on a bottom surface and a top surface which is adhered to said backing sheet;

applying a transfer sheet having a smooth surface to said adhesive coating of said backing sheet to form a sandwich;

cutting said sheet member to form an applique having a predetermined shape; and discarding of said flexible sheet.

6. A method of forming an ornamental design on a portion of a skin of a human body, said method comprising the steps of forming an applique having an adhesive surface, said applique having a predetermined non-utilitarian ornamental shape from a material capable of blocking tanning rays from a light source on a backing sheet;

applying said applique and backing sheet to the portion of the skin so that said adhesive is continuously adhered to said skin;

removing said backing sheet from said skin;

subjecting the portion of the skin to the tanning rays of the light source; and removing said applique from said skin to produce said ornamental design.

* * * * *